United States Patent [19]
Heine et al.

[11] 4,060,724
[45] Nov. 29, 1977

[54] MOUNTING APPARATUS FOR OPTICAL EXAMINATION DEVICES CONNECTED TO A PROJECTOR THROUGH A LIGHT-CONDUCTING CABLE

[75] Inventors: Helmut A. Heine; Otto H. Schmidt, both of Herrsching; Helmut W. Rosenbusch, Weilheim, all of Germany

[73] Assignees: Propper Manufacturing Company, Inc., Long Island City, N.Y.; Optotechnik Heine KG, Herrsching, Germany

[21] Appl. No.: 703,365

[22] Filed: July 8, 1976

[30] Foreign Application Priority Data
July 24, 1975 Germany .............................. 2533145

[51] Int. Cl.$^2$ ............................................ F21L 15/16
[52] U.S. Cl. ..................................... 362/32; 128/398; 211/DIG. 1; 362/398; 248/206 A
[58] Field of Search ................. 240/41.15, 52.1, 52 R, 240/1 LP, 52.15; 128/2 T, 6, 398; 248/206 R, 206 A, 309 R, 314; 211/1, 1.3, 4, 13, DIG. 1; 32/DIG. 7, 22

[56] References Cited
U.S. PATENT DOCUMENTS

| 1,459,104 | 6/1923 | Johnson | 248/314 |
| 3,758,951 | 9/1973 | Scrivo et al. | 240/41.15 X |

Primary Examiner—R. L. Moses
Attorney, Agent, or Firm—Amster & Rothstein

[57] ABSTRACT

A mounting apparatus is provided for an optical examination device secured to a hand grip at the distal end of a light-conducting cable which is connected at its near end to a projector. The mounting apparatus includes a lower mount for supporting the cable receiving end of the hand grip, which mount has a slit in it to permit passage of the cable, and an upper mount which serves as a holding device for either the other end of the hand grip or the optical examination device secured thereto. A sensing device is provided in the upper mount to turn off the light source which illuminates the cable when the hand grip is placed in the mounting apparatus and to turn the source on when the hand grip is removed from the mounting apparatus.

8 Claims, 4 Drawing Figures

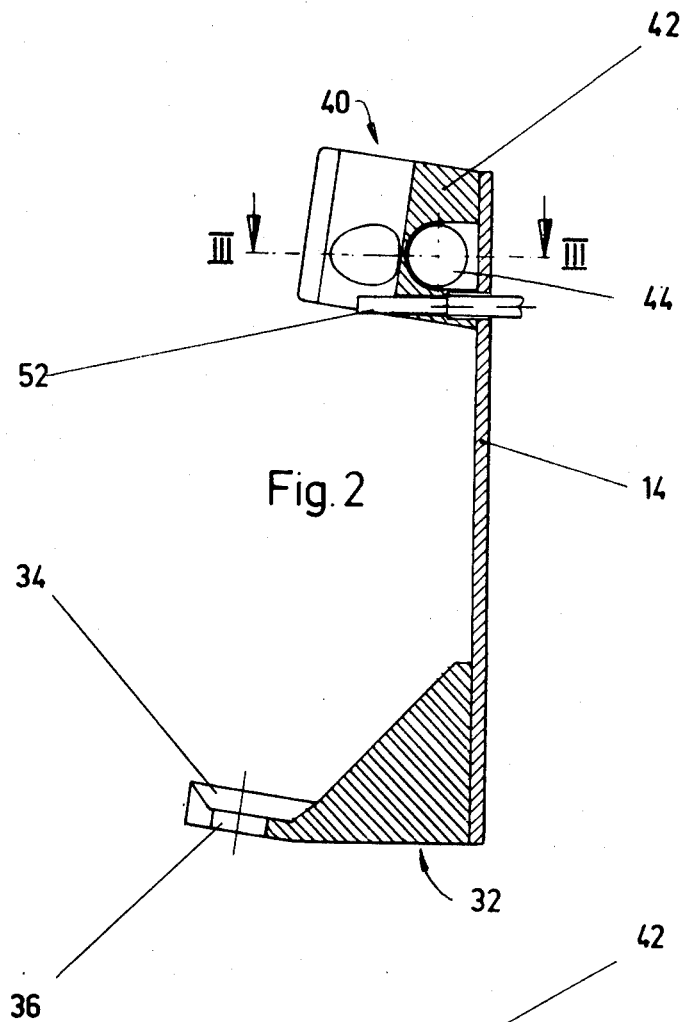
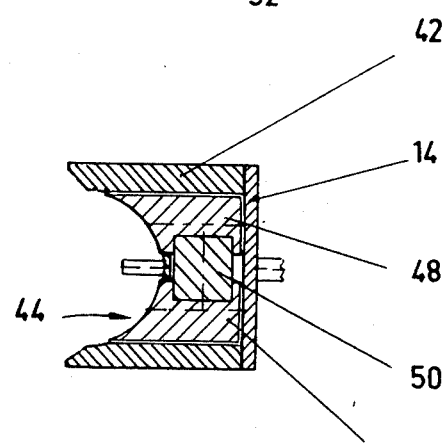

MOUNTING APPARATUS FOR OPTICAL EXAMINATION DEVICES CONNECTED TO A PROJECTOR THROUGH A LIGHT-CONDUCTING CABLE

The invention concerns a mounting apparatus for optical examination devices connected to a cold light projector through a light-conducting cable.

In medical diagnostic technology, for example for endoscopy, ophthalmoscopy, and otoscopy, so-called cold light projectors are becoming ever more popular. With these projectors, the light is guided from the projector lamps to the examination device via a light-conducting cable. By means of heat filters, the heat radiation is filtered out of the radiation entering the light-conducting cable. Another fraction of the heat radiated by the lamp is absorbed in the light-conducting cable, so that practically only radiation of the visible spectral region enters the examination device. This radiation is also designated as "cold light".

When a patient is examined and treated, such optical examination devices are only required for a short itme; in the meantime they must be available ready for access and ready for operation, so that the physician can grasp them quickly and reliably, if necessary even in the dark.

Up to now, the examination devices were placed on a cloth on a table next to the cold light projector or on the storage surface of a central examination unit. But this procedure has the disadvantage that the device can easily fall down from where it has been deposited. At the very least, it can thus be soiled if not damaged or destroyed.

A well-known fork-shaped mount could be used to secure the examination devices by setting the device or its handle therein. However, such mounts have the disadvantage that the device must be set into the mount very carefully and purposefully, and this procedure makes unnecessary demands on the time and attention of the physician.

The invention is therefore based on the task of creating a mounting apparatus for optical examination devices connected to a cold light projector. This apparatus will guarantee a secure mount for the device, and it will be possible to set the device quickly and reliably into the mount even with casual handling.

According to the invention, the mounting apparatus for optical examination devices connected to a cold light projector is characterized by a lower mount that is provided with a slit. This lower mount serves to accept the end of the examination device hand grip which receives the light conducting cable from the projector. It is further characterized by an upper mount against which the hand grip or the examination device can be rested.

The examination device can quickly and reliably be set into the mounting apparatus according to the invention, without making particular demands on the attention of the user. Furthermore, the device is retained securely, and insertion of the end of the device hand grip that carries the light conducting cable is not hindered by the light-conducting cable.

To further improve handling reliability, the holding surface of the upper mount is preferably displaced from the vertical with respect to the support surface of the lower mount, so that the device lies diagonally. Additionally or alternatively, a magnet can be inserted into the upper mount. The magnet ends at the boundary of the holding surface of the upper mount. At the same time, the hand grip or the examination device is equipped, at the level of the upper mount, with a part consisting of magnetizable material. With this design, an especially reliable support as well as easy handling are attained. The device can practically be "thrown" on the mounting apparatus.

The lifetime of projection lamps is relatively short. To prevent the projection lamps from burning continuously, a sensing pin is preferably brought out from the support surface of the lower mount or from the holding surface of the upper mount. The sensing pin is connected with a microswitch.

To save the physician the trouble of time consuming changes among several different examination devices, at least two mounting apparatuses are preferably provided.

Furthermore, the lower or upper supports or both are preferably affixed to the front plate of the cold light projector. Here the cold light projector can be placed at the edge of a table, so that the mounts extend beyond the latter. The light conducting cable can then be brought in gentle curvature downward out of the examination device and again upward to the cold light projector. For this purpose, there is no need of maintaining an especially great distance above the lower edge of the cold light projector. This is desirable, especially when the light-conducting cables used have a protective metal tube which has a relatively large minimum radius of curvature. In this way, the required contruction height can be kept so low that it can even be adapted to the limited space available for examination units.

Naturally, the mounting apparatus or mounting apparatuses can also be arranged independent of the cold light projector. Such an arrangement is, for example, suitable with an examination unit in which the cold light projector is situated at a rather large distance from the actual use location.

If the lower or upper mount of several mounting apparatuses is provided with a sensing pin that is connected to a microswitch, it is suitable to wire the two microswitches in such a way that, when they are mutually locked, only one of the two lamps can light, since only one examination device is ever required. Otherwise, the total available power would for safety reasons have to be equal to the power of all the projection lamps together.

In order also to be able to switch on the lamps individually, for example, when one mounting device is not occupied, it is preferable to provide two two-position lamp switches for switchover. Their switching contacts are connected together. Each lamp switch has a first fixed contact connected to a line that is wired to receive power before each lamp, and a second fixed contact connected to the switching contact of a two-position microswitch. One fixed contact of each of the microswitches is connected with the first fixed contact of the lamp switch, and the other fixed contact of each microswitch is connected at one connection of one of the lamps, each of which are connected to common or ground at a second connection.

So that the mounting apparatus can more easily be located in the dark, the material of the lower and/or upper mount can be transparent and can be illuminated from behind.

To avoid the necessity of having to exchange the examination device or devices completely as they are needed, only one universal hand grip is, preferably, connected to the light-conducting cable or cables. This universal hand grip contains the equipment common to the various examination devices, and various sets of supplementary equipment can be inserted into it. In this fashion, considerable costs can be saved for light-conducting cables, filters, and the like. Such costs would otherwise have to be borne separately for each examination device.

The invention will be explained in more detail by means of the preferred embodiment shown in the drawing. The following are shown:

FIG. 2 shows the vertical section through a mounting apparatus;

FIG. 3 shows the cross section III—III of FIG. 1; and

Figure 1:
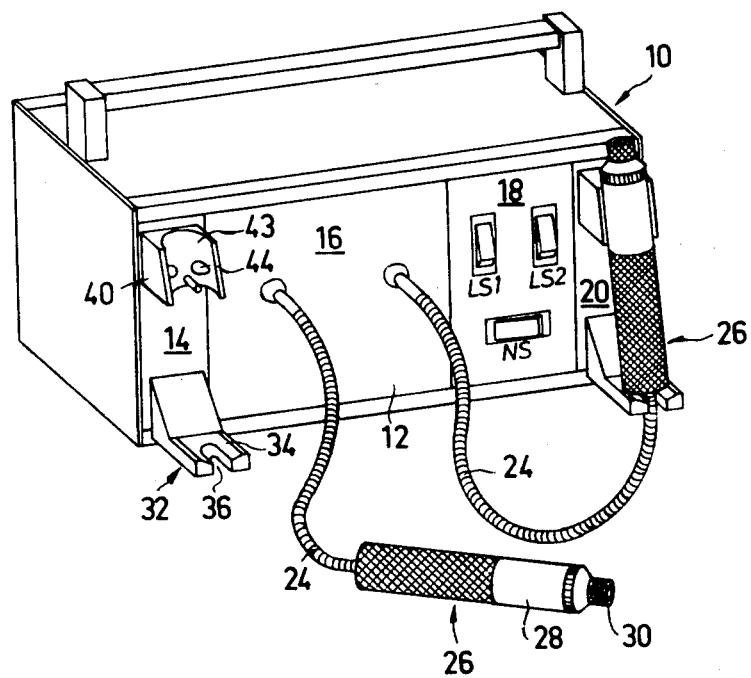
FIG. 1 shows a cold light projector with two mounting apparatuses and two universal hand grips each one of which is connected to a light-conducting cable.

FIG. 1 shows a cold light projector 10 having a front plate 12 divided into various fields, namely two mounting fields 14 and 20, a lamp field 16, and a switching field 18. These are preferably designed as plug-ins, at least in part. This is especially recommended for the lamp field 16, since this contains the most sensitive parts of the device, namely the lamps.

Two light conducting cables 24a and 24b are brought out of the lamp field 16. At their far end, each one has a universal hand grip 26a and 26b respectively connected to it. The universal hand grips 26a and 26b are each equipped with a steel cylinder 28 and a head 30. The examination equipment is inserted into the head 30 and is secured, for example, by means of a bayonet lock.

Two lamp switches LS 1 and LS 2 are provided in the switching field 18. The individual lamps can be switched by means of these lamp switches. Furthermore, a line switch NS is arranged in the lamp field. By means of this line switch, the entire electrical portion of the projector can be switched off.

One console-shaped lower mount 32 is provided on each of the mounting fields 14 and 20. This lower support 32 has a support surface 34 for the lower end of the universal hand grip 26a and/or 26b, and a slit 36. The light cable 24 is brought through the slit 36, as shown in the right part of FIG. 1. The light-conducting cable 24 can therefore hang down freely and without hindrance.

Furthermore, an upper mount 40 is fastened in each of the mounting fields 14 and 20. This upper mount 40 consists of a housing 42 (FIGS. 2 and 3) which forms an injection moulded part. The holding or receiving surface 43 of the upper mount 40 is adapted to the shape of the universal hand grip. The upper and lower mount can be designed in unit construction, for example they can consist of an injection moulded part.

As is shown schematically in FIG. 1 and in detail in FIGS. 2 and 3, a magnet 44 is mounted in a floating position in the upper mount 40. The magnet 44 essentially consists of a bar magnet 50 and two pole shoes 46 and 48. The two pole shoes are arranged approximately U-shaped.

The ends of the pole shoes 46 and 48 which point toward the holding surface 43 are adapted to the shape of the holding surface 43 of the upper mount 40.

A sensing pin 52 is brought through the upper mount 40. The sensing pin 52 extends from the holding surface 43 of the upper mount. It activates a microswitch which is not shown and which is arranged behind the mounting fields 14 and 20. When the universal hand grip is set into the mounting apparatus, the associated projection lamp is switched off, and when the universal hand grip is taken out it is switched on.

Figure 4:
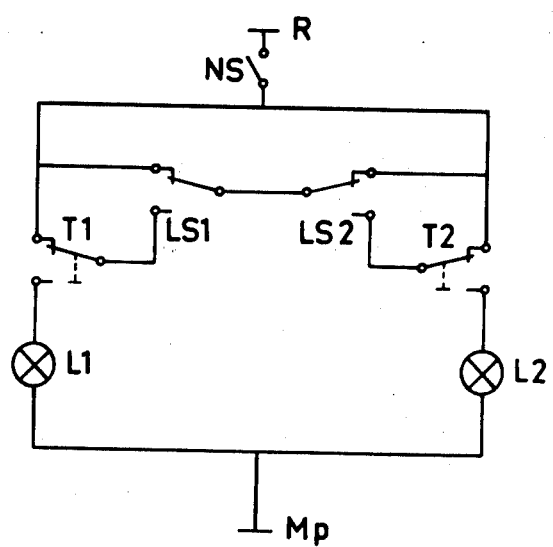
FIG. 4 shows the circuit diagram of the lamps, the microswitches, and the lamp switches.

FIG. 4 shows the circuit diagram of projection lamps L1 and L2, microswitches T1 and T2, lamp switches LS1 and LS2, all of which are designed as change-over switches, as well as the line switch NS.

The line switch NS is first connected to the bus bar R. The second terminal of the latter is connected to a fixed contact of each of the microswitches T1 and T2. The second fixed contact of the microswitches T1 and T2 is connected to the projection lamps L1 and L2. The second terminal of the projection lamps L1 and L2 is brought to the midpoint bar.

When using low voltage lamps, the line switch NS can naturally be located before the transformer of the device. In this case, the bus bar R is directly connected to the first contacts of the microswitches T1 and T2.

The switching contacts of the microswitches T1 and T2 are each connected to a fixed contact of the lamp switches LS1 and LS2 respectively. The other fixed contact of the two lamp switches LS1 and LS2 is brought to the connection between the line switch NS and the first contacts of the microswitches T1 and T2. The switching contacts of the lamp switches LS1 and LS2 are directly connected together. All switches are shown in their OFF position.

Alternate use of the two universal hand grips 26a and 26b would be the case as a rule. If such use is intended, the hand grip 26a is associated with lamp L1 and the hand grip 26b is associated with lamp L2, and the lamp switches LS1 and LS2 are switched on. If the universal hand grip 26a is now removed from its mounting apparatus 32, 40, the microswitch T1 is switched on through the sensing pin 52, and lamp L1 is therewith switched on. At the same time, lamp L2 remains switched off. If the universal hand grip 26b is also removed, possibly by mistake, lamp L2 and lamp L1 are both switched off, and an overload of the transformer is thereby avoided.

However, if the device is to be continuously or at intervals operated with only one universal hand grip, for example, only with hand grip 26a, this would be impossible while the second hand grip 26b is missing, as long as the lamp switch LS2 is switched on. If the lamp switch LS2 is now switched off, while the lamp switch LS1 remains switched on, the universal grip 26a can be used with the lamp L1, whereby the automatic switch-on and switch-off remains intact whenever the handle is removed or inserted.

Although a specific embodiment of the invention has been described for illustrative purposes, it will be appreciated by one skilled in the art that many additions, modifications and substitutions are possible without departing from the scope and spirit of the invention.

What is claimed is:

1. A mounting apparatus for an optical examination instrument, said instrument being connected at the distal end of a light-conducting cable coupled to a source of light at its near end, said apparatus comprising:
 a lower mount adapted to support said instrument at the lower end thereof, said lower mount having a slit therein for the passage of said light-conducting cable; and
 an upper mount serving as a holding device for said instrument, the end of said instrument connected to said light-conducting cable being supported on said lower mount, and an upper portion of said instrument being held in said upper mount.

2. A mounting apparatus according to claim 1 wherein said upper mount includes a holding surface displaced from the vertical with respect to said lower mount, so that said hand grip rests in a diagonal position.

3. A mounting apparatus according to claim 1 wherein said upper mount includes a holding surface having a magnet therein, said instrument being provided at the level of said upper mount with a part including magnetizable material.

4. A mounting apparatus according to claim 1 further comprising:
   switching means connected to turn said light source on and off; and
   sensing means in said mounting apparatus, responsive to the mounting of said instrument therein, for operating said switching means, so that said light source is turned off when said instrument is mounted and is turned on when said instrument is removed from said mounting apparatus.

5. In combination with a cold-light projector including a plurality of light-conducting cables each connected at its near end to a source of light in said projector and having a hand grip at its distal end adapted to receive an optical examination device, a plurality of mounting apparatuses according to claim 1, each dedicated to mounting the hand grip connected to a different one of said light-conducting cables and an optical examination device receivable thereon, the lower mount and upper mount of each mounting apparatus being secured to said projector.

6. The combination of claim 5 further including:
   switching means connected with the light source corresponding to each light-conducting cable for turning said light source on and off; and
   sensing means in each mounting apparatus, responsive to the placement of a hard grip therein, for operating the corresponding switching means, so that a light source is turned off when a hand grip is mounted in the corresponding mounting apparatus and is turned on when the hand grip is removed therefrom.

7. The combination of claim 6 wherein said switching means are connected so that only one of said light sources can be illuminated at a time.

8. In combination with a cold-light projector including two light-conducting cables each connected at its near end to a source of light in said projector and having an optical examination instrument at its distal end:
   a pair of mounting apparatuses according to claim 1, each dedicated to mounting said instrument thereon, the lower mount and upper mount of each of said mounting apparatuses being secured to said projector;
   a line wired to receive power;
   a pair of two position microswitches each having a switching contact operable between an OFF fixed contact and an ON fixed contact, each of said OFF fixed contacts being connected to said line, each of said light sources being connected between the ON fixed contact of a corresponding microswitch and a common connection;
   a pair of lamp switches each having a switching contact operable between an OFF fixed contact connected to said line and an ON fixed contact connected to the switching contact of a corresponding one of said microswitches, the switching contacts of said lamp switches being connected together; and
   sensing means in each mounting apparatus, responsive to the placement of said instrument therein, for moving the switching contact of the corresponding microswitch to its OFF fixed contact, said switching contact being moved to the ON fixed contact when said instrument is removed.

* * * * *